(12) United States Patent
Wagner

(10) Patent No.: US 6,723,372 B1
(45) Date of Patent: Apr. 20, 2004

(54) METHOD FOR PRODUCING ENCASED SPHERICAL GRANULAR GRAINS

(75) Inventor: Torsten Wagner, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/622,811

(22) PCT Filed: Feb. 24, 1999

(86) PCT No.: PCT/EP99/01100

§ 371 (c)(1),
(2), (4) Date: Aug. 23, 2000

(87) PCT Pub. No.: WO99/43303

PCT Pub. Date: Sep. 2, 1999

(30) Foreign Application Priority Data

Feb. 24, 1998 (DE) .......................... 198 08 634

(51) Int. Cl.⁷ ............................. B05D 1/02; B05D 3/02; A61K 9/24
(52) U.S. Cl. .................... 427/2.14; 427/2.15; 427/2.16; 427/2.19; 427/2.21; 427/212; 427/213; 427/213.3; 427/213.31; 427/421; 427/372.2; 427/379
(58) Field of Search ................. 427/2.14, 421, 427/2.15, 2.16, 2.19, 2.21, 212, 213, 213.3, 213.31, 372.2, 379

(56) References Cited

U.S. PATENT DOCUMENTS

| 5,286,493 A | | 2/1994 | Oshlack et al. | |
|---|---|---|---|---|
| 5,286,494 A | * | 2/1994 | Fechner et al. | 424/490 |
| 5,376,384 A | | 12/1994 | Eichel et al. | |
| 5,575,987 A | * | 11/1996 | Kamei et al. | 424/451 |
| 5,958,458 A | * | 9/1999 | Norling et al. | 424/490 |

FOREIGN PATENT DOCUMENTS

| DE | 36 22 487 | 1/1988 |
|---|---|---|
| GB | 1 251 115 | 10/1971 |
| WO | 87 05294 | 9/1987 |
| WO | 98 10751 | 3/1998 |

OTHER PUBLICATIONS

Shun Por Li et al. "Preparation and in vitro evaluation of a controlled release drug delivery system of Theopyline using an aqueous acrylic resin dispersion" Drug Develop. and Indus. Pharm. Bd. 15, Nr. 8, 1989 pp. 1231–1242.

* cited by examiner

Primary Examiner—Shrive P. Beck
Assistant Examiner—Jennifer Kolb Michener
(74) Attorney, Agent, or Firm—Millen, White, Zelano & Branigan, P.C.

(57) ABSTRACT

A process for the production of encased, spherical granular grains comprising spraying grains which consist of a prostane derivative and a cyclodextrin vehicle, forming together a prostane-cyclodextrine-clathrate, with an aqueous polymer dispersion of ethyl cellulose and/or poly(methyl)acrylic acid ester in a fluidized or boiling bed is disclosed. The polymer dispersion is applied in a thickness equivalent to 1–5% (w/w) of the total mass of the encased grains. The coated grains are cured for at least 24 hours. Grains produced according to this method have a pharmaceutical active ingredient release profile which remains unchanged over the storage time.

12 Claims, No Drawings

METHOD FOR PRODUCING ENCASED SPHERICAL GRANULAR GRAINS

The invention relates to a process for the production of encased, spherical granular grains, especially for compositions with prostane derivatives.

PRIOR ART

Prostane derivatives and their product are described in detail in EP 0 011 591 (date of application: Oct. 18, 1979). The prostane derivatives are compounds that are derived from prostacyclin ($PGl_2$). They contain a methylene group at the position of the 9-ether-oxygen atom in prostacyclin. Prostane derivatives are used for treating various diseases, whereby the cardiovascular and thromboaggregation-inhibiting action is clearly emphasized. The use of prostane derivatives as medication is described in detail in European Publication EP 0 011 591. In the publications EP 0 055 208, EP 0 099 538 and EP 0 119 949, carbacyclin derivatives are cited that have indications similar to the above-mentioned prostane derivatives. Other prostane derivatives are described in publication EP 0 084 856, which was proposed for the use in the inhibition of thrombocyte-aggregation, lowering of the systemic blood pressure or treatment of gastric ulcers. Iloprost is the most important prostane derivative.

Iloprost oral (pharmaceutical active ingredient: 5-(E)-(1S, 5S,6R)-7-hydroxy-6[(E)-(3S,4RS)-3-hydroxy-4-methyl-1-octen-6-inyl]bicyclo[3.3.0]octen-3-ylidene pentanoic acid) is a timed-release capsule. Timed-release capsules include the multiparticulate dosage form (multiple units). They consist of a hard gelatin capsule, which is filled with many small timed-release elements (in the case of iloprost oral: coated pellets [=spherical granular grains]). After peroral administration, the hard gelatin capsule is dissolved quickly in the stomach, and the individual timed-release elements are released. Regardless of how full the stomach is, from there they move on into the intestine. At the same time, the active ingredient that is contained is continuously released. Diffusion pellets represent the most important group of the coated multiparticulate dosage forms.

As coating materials for peroral timed-release dosage forms, polymers have gained tremendous importance. The polymer types that are used are primarily ethyl cellulose or poly(meth)acrylic acid ester. The polymers can be used either as an organic solution or dispersed inaqueous phase. Since they are more environmentally friendly, more reliable and more economical in handling, aqueous polymer dispersions are increasingly used in the industry. The best-known trade names are Aquacoat ECD 30®, Surelease® or Eudragit® NE 30 D, RL 30 D and RS 30 D. In the paint suspensions that are used for the coating process, additional additives are contained that are necessary for production and application reasons and help determine the properties of the film agent.

In a processing manner, the encasing process of pellets is carried out with a polymer membrane in fluidized-bed devices. By a stream of air, the pellets are arranged in a fluidized bed or a boiling bed, on which the polymer dispersion with the added additives is sprayed depending on the type of device in countercurrent or co-current flow (top or bottom spraying) from a spraying device (one or more spray nozzles). By the motion in the fluidized bed, the fine-particle dispersion is dispersed on the surface of the pellets. At the same time, the dispersing agent evaporates water by the drying stream of air, and the latex particles approach a spherical packing that becomes tighter and tighter. Then, an increasing penetration of the particles below one another takes place. This process is referred to as coalescence. In the final stage of this process, an almost homogenous, water-insoluble film develops. The film that now surrounds the pellet acts as a diffusion barrier for the pharmaceutical substance that is found in the core and results in a delayed release of pharmaceutical substance.

The production of iloprost oral is performed in two essential steps. In the first step, active ingredient-containing crude pellets are produced via an extrusion/spheronization process. The crude pellets consist of 90% lactose and 10% Avicel PH 101 as adjuvants and contain iloprost-β-cyclodextrin clathrate as an active ingredient. The content is 0.05 or 0.1 mg of iloprost per 65 or 130 mg of pellets [active ingredient content about 0.08% (w/w)]. In a second step, the crude pellets are then coated with a coating suspension that is based on Eudragit NE 30 D and additives in a fluidized-bed device.

At the beginning of the development, the crude pellets were sprayed in a fluidized-bed device (WSG), type GPCG-3 (Glatt Company)) or Strea type (Aeromatic Company) on a laboratory scale (both top-spraying processes) in principle with the qualitatively identical coating suspension, which is still used even now. As a target value for the paint layer, the resulting active ingredient-release profile was used (determined from the amount of active ingredient released after, e.g., 1, 2 and 3 hours), which was studied in the dissolution test according to USP, device 1 (basket). The pellets that were produced were used for first kinetic and clinical studies. A problem from the start was the fact that in this formulation, the release of active ingredient slowed down somewhat over the storage time. The first sizeable batches (production scale) were coated in WSG aeromatic MP4 (Aeromatic Company). Just as in the smaller laboratory devices, the spraying application took place by a countercurrent process (top spraying). In this case, it was sprayed from a spray nozzle from above in opposite direction to the incoming stream of air on the pellets located in the fluidized bed. In each case, 75 kg of active ingredient-containing crude pellets with 16.5 kg of paint suspension were ultimately sprayed in Aeromatic MP4.

The transfer of the process from the laboratory scale to the Aeromatic MP4 then revealed that the release of active ingredient slowed down over the storage time and for this reason, the batches first produced with amounts of coating larger than 16.5 kg were soon no longer able to meet the specification. This phenomenon that was noted for this formulation is described in the poster publication by T. C. WAGNER and S. KEITEL, The Effect of Dispersion Concentration and Curing Temperature on Drug Release of Pellets Coated with Eudragit NE 30 D, Proc. 1st World Meeting APGI/APV, Budapest, May 9–11, 1995. To this end, the effect of subsequent heat treatment (stoving—"curing") on the release of active ingredients was studied for the first time. For the production scale, however, no attempt at stoving was generally made, since no drying ovens were available; the exact extent of this problem was still not known and in addition basic concerns problem was still not known and in addition basic concerns existed due to the thermal instability of the active ingredient. For this reason, for production an amount of coating had to be applied that led to a post-production active ingredient-release profile that did not fall within the specification. After about four weeks of storage time at room temperature, the release had slowed, and the WSF-profile was in the upper third of the specification. Over the storage time, however, a further slowing occurred.

In the publication of F. W. GOODHART et al. (1984), An Evaluation of Aqueous Film-forming Dispersions for Controlled Release, in Pharmaceutical Technology, Vol. pp. 65–71, processes are described in which the stoving takes place for scientific purposes. The idea is to grasp the principles underlying the phenomena. The effect, to increase the stability, is not mentioned.

In the publication of Shun Por Li et al. (1989) Preparation and In Vitro Evaluation of a Controlled Release Drug Delivery System of Theophylline Using an Aqueous Acrylic Resin Dispersion, in Drug Development and Industrial Pharmacy, Vol. 15(8), pp. 1231–1242, a stoving is described in which the active ingredient theophylline is encased with poly(meth)acrylic acid ester. The stoving is carried out at 40° C. for 24 hours. The stability is increased in the case of this active ingredient by the stoving.

Object and Achievement

The object is to offer a process for the production of a shell for spherical granular grains, with which an active ingredient-release profile can be obtained, and which lies within the specification even after an extended storagetime.

The object is achieved by a process for the production of encased, spherical granular grains (pellets), Whereby the process comprises the following steps:

α) in a fluidized bed or boiling bed, active ingredient-containing crude pellets that consist of at least one pharmaceutical active ingredient and optionally pharmaceutically compatible additives and/or vehicles are sprayed with a polymer dispersion and additives, which comprises an ethyl cellulose and/or a poly(meth)acrylic acid ester as a polymer, β) a polymer dispersion is applied with a polymer thickness in the range of 1 to 5% (w/w) of the total mass, whereby the total mass corresponds to the composition of the encased pellets, γ) the pellets that are encased with polymer are stoved at a temperature of 45 to 65° C., δ) the stoving of the pellets that are encased with the polymer lasts for at least 24 hours, and ε) the pharmaceutical active ingredient is a prostane derivative.

Preferred is a fluidized bed or a boiling bed in which the pellets are sprayed in a co-current process. More preferred is a co-current process in which the polymer dispersion (and added additives) is sprayed into the fluidized bed or the boiling bed from at least 1 or 2, preferably 12 nozzles.

It is preferred that the polymer dispersion comprise either ethyl cellulose or a poly(meth)acrylic acid ester as polymer.

It is advantageous if the thickness of the applied polymer is dispersed uniformly over the pellet. The tolerances of the polymer thickness should advantageously be only ±30%, preferably ±20% and more preferably ±10%.

Preferred is a process according to the invention, in which the encased pellets are then moved into a tablet or a timed-release capsule, which are, for example, hard gelatin capsules. Filling in capsules is preferred. Other filling devices or containers of encased pellets are also possible. Such containers can be present in IUDs, which release a steroid in a delayed fashion there. The filling devices can also be used as tablets with easily detached molding materials. In addition, containers are possible as implants.

Preferred is a process according to the invention in which the pellets as active ingredients comprise prostane derivatives and pharmaceutical vehicles and/or additives. Also preferred are low-dosed active ingredients, such as, for example, steroids (active ingredient content less than 1%). Most preferred is the active ingredient 5-(E)-(1S,5S,6R)-7-hydroxy-6[(E)-(3S,4RS)-3-hydroxy-4-methyl-1-octen-6-inyl]bicyclo[3.3.0]octen-3-ylidene pentanoic acid and as an additive at least cyclodextrin.

Advantages

In optimizing phases, the stoving conditions according to the invention were developed. The stoving at 50° C. over 48 hours is suitable to stabilize in a reproducible manner the active ingredient release in the existing formulation and to keep it constant over the storage time.

The difference of the process according to the invention compared to the publication of Shun Por Li et al. (1989) Drug Development and Industrial Pharmacy, Vol. 15(8), pp. 1231–1242 consists in the fact that prostane derivatives, in contrast to theophylline, are not stabilized when they are stoved at 40° C. over 24 hours. This publication therefore describes a method that entails a substance-specific stoving. The technique that is mentioned in the document cannot be transferred to the prostane derivatives and does not result in the desired action in the case of prostane derivatives.

Preferred Embodiments

Ethyl cellulose is described in Römpp Chemie Lexikon, 9th Edition, 1990, publishers J. FALBE and M. REGITZ, Georg Thieme Verlag, Stuttgart (ISBN 3-13-734709-2) on page 1254. The citation is part of the disclosure.

Preferred as a polymer is poly(meth)acrylic acid ester, which is described in European Pharmacopeia, 3rd Edition, Deutscher Apotheker Verlag, Stuttgart, Eschborn, on page 1516 to page 1517 under Item 733. This reference is a part of the application by citation.

Most preferred as polymer is EUDRAGIT NE 30 D, which is described in the following publications:

K. LEHMANN and D. DREHER (1979) Coating Small Particles with Acrylic Resins, Pharmaceutical Technology, Vol. 3 (3);

K. LEHMANN (1984) Formulation of Controlled Release Tablets with Acrylic Resins, Acta Pharm. Fenn. Vol. 93, pp. 55;

K. LEHMANN, (1986) Acrylic Lattices from Redispersable Powders for Peroral and Transdermal Drug Formulations, Drug Development and Industrial Pharmacy, Vol. 12(3), pp. 265;

K. LEHMANN and D. DREHER (1986) Mischbarkeit w äBriger Poly(meth)acrylat-Dispersionen für Arzneimeitteluberzuge [Miscibility of Aqueous Poly(meth) acrylate Dispersions for Pharmaceutical Agent Coatings], Pharm. Ind. Vol. 48, pp. 1182;

K. LEHMANN and H. U. PETEREIT (1988) Verwendung wäBriger Poly(Meth)acrylat-Dispersionen für die Herstellung von Matrixtabletten [Use of Aqueous Poly (meth)acrylate Dispersions for the Production of Matrix Tablets], (1988) Acta Pharma. Tech. Vol. 34(4), pp. 189 and K. LEHMANN et al. (1989) Praktikum de, Lackdragierens [Workshop for Paint Application].

As crude pellets, the pellets comprise the pharmaceutical active ingredient and in addition pharmaceutically compatible vehicles and additives. Such vehicles and additives are described in Remington's Pharmaceutical Science, 15th Ed. Mack Publishing Company, Easton, Pa. (1980).

More preferred as a vehicle is cyclodextrin. Cyclodextrin is formed after the degradation of starch by Bacillus macerans or Bacillus circulans under the action of cyclodextrin glycosyl transferase. The cyclodextrins consist of 6, 7 or 8 α-1-4-linked glucose units (α-, β- and γ-cyclodextrins). The cyclohexa-(hepta-, octa-)amyloses are arranged in layers on one another in the crystal lattice of cyclodextrins, so that they form through-going inner-molecular channels, in which they can enclose hydrophobic molecules in differing amounts. (Literature: Adv. Carbohydr. Chem. Vol. 12, p. 189 (1987), Angew. Chem. (Applied Chemistry), Vol. 92, p. 343 (1980), Bender and Komiyama, Cyclodextrin Chemistry, Berlin: Springer 1978, Naturwissenschaften [Natural Sciences], Vol. 154, p. 625 (1967)).

The pharmaceutical active ingredient relates to prostane derivatives of general formula I or II

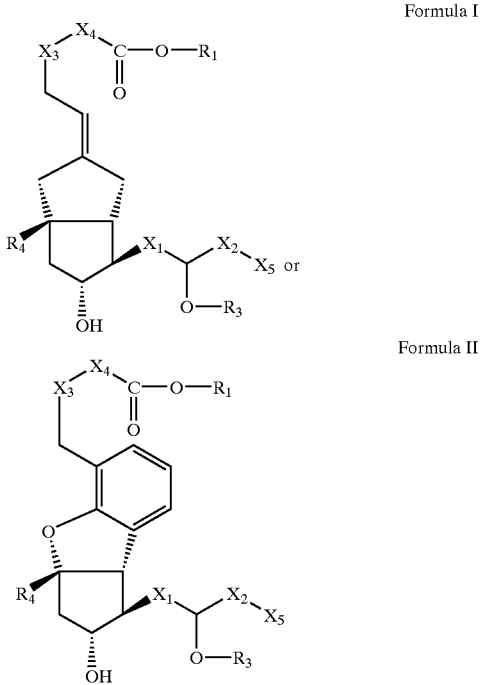

Formula I

Formula II in which $X_1$ is a —$CH_2$—$CH_2$—; trans —CH=CH— or —C≡C, $X_2$ is a straight-chain or branched saturated alkylene group with 1 to 6 carbon atoms, $X_3$ is an —O— or —$CH_2$—, $X_4$ is a —$CH_2$— or —$[CH_2]_3$—, $X_5$ is an —H or —C≡C—$R_2$;

$R_1$ is a hydrogen atom, an alkyl group with 1 to 6 carbon atoms, a cycloalkyl group with 5 or 6 carbon atoms or a phenyl group, $R_2$ is a straight-chain or branched-chain, saturated or unsaturated alkyl group with 1 to 6 carbon atoms, $R_3$ is a hydrogen atom, an acyl radical with 1 to 4 carbon atoms or a benzoyl radical, and $R_4$ is an —H or —$CH_3$;

whereby the —O—$R_3$ group is in α- or β-position, and their salts with physiologically compatible bases, if $R_1$ has the meaning of a hydrogen atom.

Publications EP 0 011 591, EP 0 055 208, EP 0 099 538, EP 0 119 949, EP 0 084 856 and EP 0 686 036 describe the prostane derivatives, their production and use. The publications are part of the disclosure relative to the substances, their production and use.

Inorganic and organic bases, as they are known to one skilled in the art for forming physiologically compatible salts, are suitable for salt formation with free acids. For example, there can be mentioned: alkali hydroxides, such as sodium and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc. The β-cyclodextrin clathrates are produced according to EP 0 259 468.

Preferred is the use of prostane derivatives according to the invention with the above-mentioned general formula I in which $X_1$ is a trans —CH=CH—, $X_2$ is a straight-chain or branched, saturated alkylene group with 2 to 4 carbon atoms, $X_3$ is a —$CH_2$—, $X_4$ is a —$CH_2$—, $X_5$ is a —C≡C—$R_2$, $R_1$ is a hydrogen atom, an alkyl group with 1 to 3 carbon atoms or a phenyl group, $R_2$ is a straight-chain or branched-chain, saturated or unsaturated alkyl group with 1 to 3 carbon atoms, $R_3$ is a hydrogen atom or an acyl radical with 2 carbon atoms, and $R_4$ is an —H, whereby the —O—$R_3$ group is in a- or b-position, and their salts with physiologically compatible bases, if $R_1$ has the meaning of a hydrogen atom.

Most preferred is the use of a prostane derivative with the name "iloprost" and which bears the systematic title 5-(E)-(1S,5S,6R)-7-hydroxy-6[(E)-(3S,4RS)-3-hydroxy-4-methyl-1-octen-6-inyl]bicyclo[3.3.0]octen-3-ylidene pentanoic acid.

In addition, it also comprises as active ingredients the substances cicaprost, eptaloprost, ciprostene and/or beraprost and salts thereof.

Pharmaceutical active ingredients can also be present as low-dosed active ingredients, in this case active ingredient contents of 1% and less (w/w) relative to the total mass of active ingredient and vehicle and additive. A percentage of 0.3 and less is preferred; a percentage of 0.1 and less is more preferred.

Preferred is a polymer thickness of 1.5 to 4% (w/w) of the total mass; more preferred is a thickness of 1.75 to 3% and most preferred is a thickness of 2.1%±10% (2.0–2.2%).

For the temperature range during stoving, the lower temperature limit of 45° C. is preferred, 47° C. is more preferred, 48° C. is still more preferred, and 50° C. is most preferred.

For the temperature range during stoving, the upper temperature limit of 65° C. is preferred, 60° C. is more preferred, 47° C. is still more preferred, and 53° C. is most preferred.

The dwell time during stoving is at least 24 hours. Comparably good results are achieved by an extended stoving. Inferior data for the active ingredient-release profile are obtained with a shortening. A high temperature can impair the stability of the product in the usual way. The shortest possible times and mild conditions during stoving are therefore desirable. Most preferred is a dwell time of 48 h±5 h.

EXAMPLES

Example 1

Prior Process, Top Spraying, Production Scale, No Stoving a) Active ingredient-containing crude pellets are produced according to an extrusion/spheronization process. For this purpose, an active ingredient-containing adjuvant/active ingredient premixture (90% lactose, 90% <0.1 mm, 10% Avicel PH 101 and iloprost-β-cyclodextrin clathrate) is granulated in a mixer with water. In a second step, the moist powder mixture is formed by the perforated disk of an extruder into a strand-like granulate, which is rounded into spherical granular grains (pellets) in the spheronizing cell. Then, the crude pellets are dried in a fluidized-bed drier.

b) 75 kg of active ingredient-containing crude pellets [active ingredient content of iloprost 0.08% (w/w)] is sprayed in a top-spraying process in an Aeromatic MP 4 coater with 16.5 kg of coating suspension of the following composition:

7.063 kg of Eudragit® NE 30 D 0.090 kg of magnesium stearate 0.066 kg of titanium dioxide 0.040 kg of polyethylene glycol 6000

0.046 kg of polysorbate 80

9.195 kg of water

For the spraying process, the following parameters are set:

| Incoming air temperature: | 35° C. |
| --- | --- |
| Spraying rate: | 235 g/min |
| Spray nozzle: | a two-substance nozzle, diameter 1.8 mm |
| Spraying air pressure: | 4 bar |

The timed-release pellets that are thus obtained have the following composition:

| | |
| --- | --- |
| 0.050 mg | of iloprost |
| 0.330 mg | of β-cyclodextrin |
| 56.260 mg | of lactose, 90% < 0.1 mm |
| 6.250 mg | of Avicel PH 101 |
| 1.777 mg | of Eudragit ® NE |
| 0.075 mg | of magnesium stearate |
| 0.055 mg | of titanium dioxide |
| 0.034 mg | of polyethylene glycol 6000 |
| 0.039 mg | of polysorbate 80 |
| 0.134 mg | of silicon dioxide |
| 65.00 mg | of timed-release pellets |

The in vitro release study of a divided dose in the dissolution test, device 1, basket, USP in phosphate buffer solution, pH 7.4, resulted in the following values:

| Time of the Study | Release after 1 Hour | Release after 2 Hours | Release after 3 Hours |
| --- | --- | --- | --- |
| Start | 64.3% | 86.8% | 95.8% |
| After 4 weeks of storage | 48.7% | 75.7% | 86.5% |
| After 3 months of storage | 42.4% | 70.9% | 85.9% |
| After 24 months of storage | 32.4% | 58.3% | 75.9% |

The storage was carried out at room temperature. The reduction of the release rates over the storage time confirms that it is not a stable product.

Example 2

Prior Process, Top Spraying, Laboratory Scale, Without Stoving and With Stoving at 50° C./4 Hours a) Active ingredient-containing crude pellets are produced as in Example 1a).

b) 750 g of active ingredient-containing crude pellets [active ingredient content of iloprost 0.08% (w/w)] is sprayed in a top-spraying process in an Aeromatic Streal— coater with 240 g of coating suspension of the following composition:

| | |
| --- | --- |
| 178.5 g | of Eudragit (®) NE 30 D |
| 2.3 g | of magnesium stearate |
| 1.7 g | of titanium dioxide |
| | of polyethylene glycol 6000 |
| 1.2 g | of polysorbate 80 |
| 232.2 g | of water |
| 416.9 g | of coating suspension |

For the spraying process, the following parameters are set:

| Incoming air temperature: | 28–32° C. |
| --- | --- |
| Spraying rate: | 4 g/min. |
| Spray nozzle: | a two-substance nozzle, diameter 1.0 mm |
| Spraying air pressure: | 1.0 bar |

After the coating process, a portion of the timed-release pellets is stoved at 50° C. in a circulating air drier for 4 hours.

The timed-release pellets that are thus obtained have the following composition:

| | |
| --- | --- |
| 0.050 mg | of iloprost |
| 0.330 mg | of β-cyclodextrin |
| 54.632 mg | of lactose, 90% < 0.1 mm |
| 6.113 mg | of Avicel PH 101 |
| 2.549 mg | of Eudragit (®) NE |
| 0.110 mg | of magnesiuin stearate |
| 0.979 mg | of titanium dioxide |
| 0.048 mg | of polyethylene glycol 6000 |
| 0.057 mg | of polysorbate 80 |
| 0.132 mg | of silicon dioxide |
| 65.000 mg | of timed-release pellets |

The in vitro release study of a divided dose in the dissolution test, device 1, basket, USP in phosphate buffer solution, pH 7.4 resulted in the following values:

| Time of the Study | Release after 1 Hour | Release after 2 Hours | Release after 3 Hours |
| --- | --- | --- | --- |
| Start (without stoving) | 79.8% | 97.3% | 101.1% |
| After 4 weeks of storage (without stoving) | 63.4% | 88.2% | 100.4% |

-continued

| Time of the Study | Release after 1 Hour | Release after 2 Hours | Release after 3 Hours |
|---|---|---|---|
| Start (stoved: 50° C./4 hours) | 58.7% | 85.9% | 96.7% |
| After 4 weeks of storage (stoved: 50° C./4 hours) | 49.8% | 79.2% | 94.3% |

The storage was carried out at room temperature. Both the product without stoving and the product that was stoved at 50° C. over 4 hours proved to be unstable based on the reduction of release rates over a storage time of 4 weeks.

Example 3

Modified, New Process, Bottom Spraying, Production Scale, Stoving at 50° C./4 Hours)

a) Active ingredient-containing crude pellets are produced as in Example 1a).

b) 45 kg of active ingredient-containing crude pellets [active ingredient content of iloprost 0.08% (w/w)] is sprayed in a bottom-spraying process in a Huttlin HKC 50 coater with 7.7 kg of coating suspension of the following composition:

| | |
|---|---|
| 3.297 kg | of Eudragit (®) NE 30 D |
| 0.042 kg | of magnesium stearate |
| 0.031 kg | of titanium dioxide |
| 0.019 kg | of polyethylene glycol 6000 |
| 0.021 kg | of polysorbate 80 |
| 4.290 kg | of water |
| 7.700 kg | of coating suspension |

For the spraying process, the following parameters are set:

| | |
|---|---|
| Incoming air temperature: | 32° C. |
| Spraying rate: | 200 g/min |
| Spray nozzle: | 12 three-substance nozzles, diameter 0.8 mm |
| Spraying air pressure: | 1.5 bar. |

After the coating process, a portion of the timed-release pellets is stoved at 50° C. in a circulating air drier for 4 hours.

The timed-release pellets that are thus obtained have the following composition:

| | |
|---|---|
| 0.050 mg | of iloprost |
| 0.330 mg | of β-cyclodextrin |
| 56.606 mg | of lactose, 90% < 0.1 mm |
| 6.332 mg | of Avicel PH 101 |
| 1.392 mg | of Eudragit (®) NE |
| 0.059 mg | of magnesium stearate |
| 0.044 mg | of titanium dioxide |
| 0.027 mg | of polyethylene glycol 6000 |
| 0.030 mg | of polysorbate 80 |
| 0.130 mg | of silicon dioxide |
| 65.000 mg | of timed-release pellets |

The in vitro release study of a divided dose in the dissolution test, device 1, basket, USP in phosphate buffer solution pH 7.4 resulted in the following values:

| Time of the Study | Release After 1 Hour | Release After 2 Hours |
|---|---|---|
| Start (stoved 50° C./ 4 hours) | 51.2% | 78.1% |
| After 4 weeks of storage (stoved: 50° C./4 hours) | 46.3% | 75.4% |

The storage was carried out at room temperature. As in Example 3, the product that was stoved at 50° C. over 4 hours shows a reduction in the release rates over a storage time of 4 weeks. The product is also not stable.

Example 4

New Process/Final Process, Bottom Spraying, Production Scale, Without Stoving and With Stoving at 50° C./48 Hours)

a) Active ingredient-containing crude pellets are produced as in Example 1a).

b) 45 kg of active ingredient-containing crude pellets [active ingredient content of iloprost 0.08% (w/w)] is sprayed in a bottom-spraying process in a Hüttlin HKC 50 coater with 7.6 kg of coating suspension of the following composition:

| | |
|---|---|
| 3.253 kg | of Eudragit (®) NE 30 D |
| 0.041 kg | of magnesium stearate |
| 0.030 kg | of titanium dioxide |
| 0.018 kg | of polyethylene glycol 6000 |
| 0.021 kg | of polysorbate 80 |
| 4.237 kg | of water |
| 7.600 kg | of coating suspension |

For the spraying process, the following parameters are set:

| | |
|---|---|
| Incoming air temperature: | 32° C. |
| Spraying rate: | 200 g/min |
| Spray nozzle: | 12 three-substance nozzles, diameter 0.8 mm |
| Spraying air pressure: | 1.5 bar |

After the coating process, the timed-release pellets are stoved at 50° C. in a circulating air drier for 48 hours.

The timed-release pellets that are thus obtained have the following composition:

| | |
|---|---|
| 0.050 mg | of iloprost |
| 0.330 mg | of β-cyclodextrin |
| 56.628 mg | of lactose, 90% < 0.1 mm |
| 6.334 mg | of Avicel PH 101 |
| 1.374 mg | of Eudragit (®) NE |
| 0.058 mg | of magnesium stearate |
| 0.042 mg | of titanium dioxide |

-continued

| | |
|---|---|
| 0.025 mg | of polyethylene glycol 6000 |
| 0.030 mg | of polysorbate 80 |
| 0.129 mg | of silicon dioxide |
| 65.000 mg | of timed-release pellets |

The in vitro release study of a divided dose in the dissolution test, device 1, basket, USP in phosphate buffer solution pH 7.4 resulted in the following values:

| Time of the Study | Release After 1 Hour | Release After 2 Hours | Release After 3 Hours |
|---|---|---|---|
| Start (stoved: 50° C./48 hours) | 49.8% | 74.6% | 86.5% |
| Storage after 4 weeks (stoved: 50° C./48 hours) | 49.3% | 75.1% | 87.2% |
| Storage after 9 months (stoved: 50° C./48 hours) | 49.4% | 71.4% | 84.2% |

The storage was carried out at room temperature. The product that is stoved at 50° C. over 48 hours is also stable after a storage time of 9 months.

What is claimed is:

1. A process for the production of encased, spherical granular grains comprising:
   (a) spraying crude grains, which consist of at least one prostane derivative as pharmaceutical active ingredient and cyclodextrin as a vehicle, which form together a prostane-cyclodextrine-clathrate, and optionally pharmaceutically compatible additives and/or vehicles, with an aqueous polymer dispersion and additives which comprise an ethyl cellulose and/or a poly(meth) acrylic acid ester as a polymer, in a fluidized bed or boiling bed,
   (b) applying said polymer dispersion to obtain a polymer thickness in the range of 1 to 5% (w/w) of the total mass and wherein the total mass corresponds to the composition of the encased grains, and
   (c) curing the grains that are encased with said polymer dispersion at a temperature of 45 to 65° C. for at least 24 hours and
      wherein said grains have a pharmaceutical active ingredient release profile which remains unchanged over the storage time.

2. The process according to claim 1, wherein the grains are sprayed in a co-current process.

3. The process according to claim 2, wherein the polymer dispersion and optionally added additives are sprayed into the fluidized bed or boiling bed from at least 1 nozzle.

4. The process according to claim 1, wherein the encased grains are formulated in a time-release capsule or tablet.

5. The process according to claim 1, wherein the active ingredient comprises 5-(E)-(1S,5S,6R)-7-hydroxy-6[(E)-(3S,4RS)-3-hydroxy-4-methyl-1-octen-6-inyl]bicyclo[3.3.0] octen-3-ylidenepentanoic acid and the vehicle is β-cyclodextrin and said iloprost is present as a iloprost-β-cyclodextrin-clathrate.

6. The process according to claim 1, wherein the pharmacutical active ingredients are present as low-dosed active ingredients.

7. The process according to claim 1, wherein said polymer dispersion has a thickness of 1.5 to 4% (w/w) of the total mass.

8. The process according to claim 1, wherein the curing temperature is 45 to 60° C.

9. The process according to claim 1, wherein the curing lasts 43 to 53 hours.

10. A process for the production of encased, spherical granular grains, with sustained pharmaceutical active ingredient release profiles which remain unchanged over the storage time, comprising:
   (a) spraying crude grains, which consist of at least one prostane derivative as as pharmaceutical active ingredient and cyclodextrin as a vehicle, which form together a prostane-cyclodextrine-clathrate, and optionally pharmaceutically compatible additives, with an aqueous polymer dispersion and additives which comprise an ethyl cellulose and/or a poly(meth) acrylic acid ester as a polymer, in a fluidized bed or boiling bed,
   (b) applying said polymer dispersion to obtain a polymer thickness in the range of 1 to 5% (w/w) of the total mass and wherein the total mass corresponds to the composition of the encased grains, and
   (c) curing the grains that are encased with said polymer dispersion at a temperature of 45 to 65° C. for at least 24 hours, after the grains are dried.

11. The process according to claim 10, wherein the prostane derivative is a 5-(E)-(1S,5S,6R)-7-hydroxy-6[(E)-(3S,4RS)-3-hydroxy-4-methyl-1-octen-6-inyl]bicyclo[3.3.0] octen-3-ylidenepentanoic acid.

12. The process according to claim 1, wherein said process is coalescence.

* * * * *

UNITED STATES PATENT AND TRADEMARK OFFICE
CERTIFICATE OF CORRECTION

PATENT NO. : 6,723,372 B1
DATED : April 20, 2004
INVENTOR(S) : Torsten Wagner

It is certified that error appears in the above-identified patent and that said Letters Patent is hereby corrected as shown below:

Column 12,
Line 12, reads "P-cyclodextrin" should read -- β-cyclodextrin --
Lines 14-15, reads "pharmacutical" should read -- pharmaceutical --

Signed and Sealed this

Twenty-eighth Day of June, 2005

JON W. DUDAS
*Director of the United States Patent and Trademark Office*